United States Patent
Senda et al.

(10) Patent No.: US 7,615,660 B2
(45) Date of Patent: Nov. 10, 2009

(54) PRODUCTION PROCESS OF ALKOXY-TITANIUM COMPLEX

(75) Inventors: Taichi Senda, Takatsuki (JP); Hidenori Hanaoka, Suita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 21 days.

(21) Appl. No.: 11/883,242

(22) PCT Filed: Jan. 24, 2006

(86) PCT No.: PCT/JP2006/301397

§ 371 (c)(1), (2), (4) Date: Jul. 26, 2007

(87) PCT Pub. No.: WO2006/080479

PCT Pub. Date: Aug. 3, 2006

(65) Prior Publication Data

US 2008/0306293 A1    Dec. 11, 2008

(30) Foreign Application Priority Data

Jan. 28, 2005  (JP)  ............... 2005-020958
Jan. 28, 2005  (JP)  ............... 2005-020963

(51) Int. Cl.
C07F 17/00   (2006.01)
C07F 7/28    (2006.01)

(52) U.S. Cl. ............... 556/11; 556/12; 556/53; 556/54

(58) Field of Classification Search ............... 556/11, 556/12, 53, 54
See application file for complete search history.

(56) References Cited

U.S. PATENT DOCUMENTS 6,090,961 A * 7/2000 Hanaoka et al. ............... 556/11
7,141,690 B2 * 11/2006 Hanaoka et al. ............... 556/52

FOREIGN PATENT DOCUMENTS

| EP | 0 970 964 A2 | 1/2000 |
|---|---|---|
| JP | 45-2395 B | 1/1970 |
| JP | 54-59265 A | 5/1979 |
| JP | 58-19309 A | 2/1983 |
| JP | 9-87313 A | 3/1997 |
| JP | 2000-86678 A | 3/2000 |
| JP | 2000-119286 A | 4/2000 |
| JP | 2000-119287 A | 4/2000 |
| JP | 2004-339137 A | 12/2004 |

* cited by examiner

Primary Examiner—Porfirio Nazario Gonzalez
(74) Attorney, Agent, or Firm—Birch, Stewart, Kolasch & Birch, LLP

(57) ABSTRACT

The present invention provides a process for producing an alkoxy-titanium complex of formula (2) by reacting a titanium halide complex of formula (1) with an alkaline earth metal alkoxide:

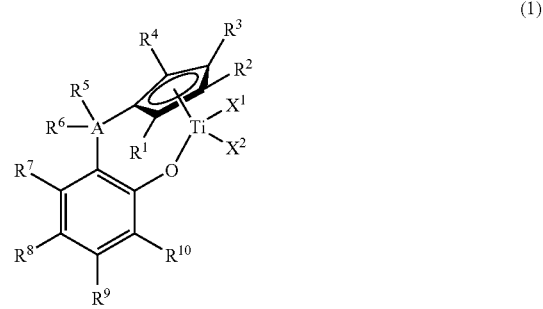

(1)

wherein A denotes a Group 14 element in a periodic table; $R^1$, $R^2$, $R^3$, and $R^4$ are the same or different and denote a hydrogen atom, halogen,
a $C_{1-20}$ alkyl group which may be substituted by halogen, a $C_{6-20}$ aryl group which may be substituted by halogen, or the like;
$R^5$, $R^6$, $R^7$, $R^8$, $R^9$, and $R^{10}$ are the same or different and independently denote a hydrogen atom, halogen,
a $C_{1-20}$ alkyl group which may be substituted by halogen, or the like; and $X^1$ and $X^2$ independently denote any halogen atom:

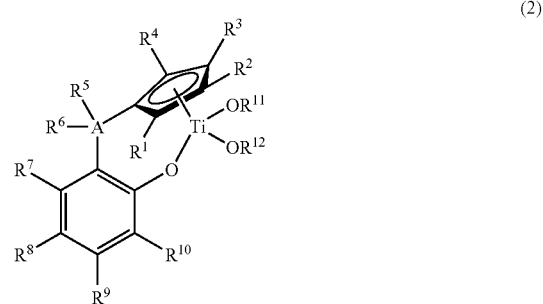

(2)

wherein $R^{11}$ and $R^{12}$ are the same or different and independently denote a $C_{1-20}$ alkyl group which may be substituted by halogen, or the like.

5 Claims, No Drawings

PRODUCTION PROCESS OF ALKOXY-TITANIUM COMPLEX

TECHNICAL FIELD

The present invention relates to a production process of an alkoxy-titanium complex.

BACKGROUND ART

Complexes of Group 4 transition metals such as titanium or zirconium are useful metal complexes in versatile organic synthetic reactions, for example, as Lewis acid in transesterification reaction or Diels-Alder reaction. For example, usability of titanium tetraisopropoxide (e.g., see Patent Document 1) and titanocene diacetate (e.g., see Patent Document 2) as transesterification catalysts is disclosed. Further, these metal complexes have extremely high industrial values as olefin polymerization catalysts and there are many reports on that. For example, production processes of olefin polymers using a metallocene complex and aluminoxane are reported (e.g., see Patent Document 3). An alkoxy-titanium complex of the present invention is a promising metal complex that is expected to exhibit specific activity due to its unique structure (e.g., see Patent Document 4) and development of an industrially advantageous production process of the complex has been desired.

Alkoxy-titanium complexes can be produced, for example, by a reaction of a corresponding titanium halide complex with an alkali metal alkoxide, or with an alcohol in the presence of a base (e.g., see Patent Document 5); however it is industrially desirable to provide a process for producing an alkoxy-titanium complex using raw materials that can be handled more safely for industrial production and can be used under more moderate reaction conditions.

[Patent Document 1] Japanese Patent Application Laid-Open (JP-A) No. 54-59265
[Patent Document 2] Japanese Patent Application Publication (JP-B) No. 45-2395
[Patent Document 3] JP-A No. 58-19309
[Patent Document 4] JP-A No. 9-87313
[Patent Document 5] JP-A No. 2000-119287

DISCLOSURE OF THE INVENTION

The present inventors have made various investigations to solve the above-mentioned problems and have found an industrially advantageous production process of an alkoxy-titanium complex and have accomplished the present invention.

That is, the present invention provides a process for producing an alkoxy-titanium complex of formula (2):

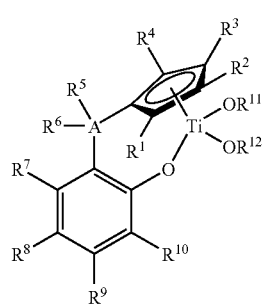

(2)

wherein A, $R^1$, $R^2$, $R^3$, $R^4$, $R^5$, $R^6$, $R^7$, $R^8$, $R^9$, and $R^{10}$ each denotes the same meaning as described below;

$R^{11}$ and $R^{12}$ are the same or different and independently denote a $C_{1-20}$ alkyl group which may be substituted by halogen, a $C_{7-20}$ aralkyl group which may be substituted by halogen, or a $C_{6-20}$ aryl group which may be substituted by halogen, and $R^{11}$ and $R^{12}$ may be arbitrarily bonded to form a ring, which comprises reacting an alkaline earth metal alkoxide with a titanium halide complex of formula (1):

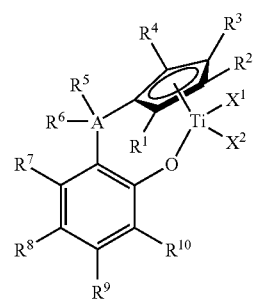

(1)

wherein A denotes a Group 14 element of the periodic table; $R^1$, $R^2$, $R^3$, and $R^4$ are the same or different and independently denote a hydrogen atom, halogen,
a $C_{1-20}$ alkyl group which may be substituted by halogen,
a $C_{6-20}$ aryl group which may be substituted by halogen,
a $C_{7-20}$ aralkyl group which may be substituted by halogen,
a silyl group substituted by $C_{1-20}$ hydrocarbon which may be substituted by halogen,
a $C_{1-20}$ alkoxy group which may be substituted by halogen,
a $C_{6-20}$ aryloxy group which may be substituted by halogen,
a $C_{7-20}$ aralkyloxy group which may be substituted by halogen,
a silyloxy group substituted by $C_{1-20}$ hydrocarbon which may be substituted by halogen,
an amino group substituted by $C_{1-20}$ hydrocarbon which may be substituted by halogen,
a phosphino group substituted by $C_{1-20}$ hydrocarbon which may be substituted by halogen, or
a thio group substituted by $C_{1-20}$ hydrocarbon which may be substituted by halogen;
$R^5$, $R^6$, $R^7$, $R^8$, $R^9$, and $R^{10}$ are the same or different and independently denote a hydrogen atom, halogen,
a $C_{1-20}$ alkyl group which may be substituted by halogen,
a $C_{1-20}$ alkoxy group which may be substituted by halogen,
a $C_{6-20}$ aryl group which may be substituted by halogen,
a $C_{6-20}$ aryloxy group which may be substituted by halogen,
a $C_{7-20}$ aralkyl group which may be substituted by halogen,
a $C_{7-20}$ aralkyloxy group which may be substituted by halogen,
a silyl group substituted by $C_{1-20}$ hydrocarbon which may be substituted by halogen, or
an amino group substituted by $C_{1-20}$ hydrocarbon which may be substituted by halogen;
neighboring groups among $R^1$, $R^2$, $R^3$, and $R^4$ may be arbitrarily bonded to form a ring and $R^5$ and $R^6$ may be bonded to form a ring; neighboring groups among $R^7$, $R^8$, $R^9$, and $R^{10}$ may be arbitrarily bonded to form a ring, and $X^1$ and $X^2$ independently denote any halogen atom.

BEST MODES FOR CARRYING OUT THE INVENTION

Hereinafter, the present invention will be described in detail.

Examples of a group having a cyclopentadienyl type anionic skeletal structure of formula (5):

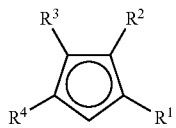

wherein $R^1$, $R^2$, $R^3$, and $R^4$ independently denote the same meaning as described above, in the titanium halide complex of formula (1) (hereinafter abbreviated as titanium halide complex (1)) and the alkoxy-titanium complex of formula (2) (hereinafter abbreviated as alkoxy-titanium complex (2)), include, for example, a cyclopentadienyl group, a methylcyclopentadienyl group, a dimethylcyclopentadienyl group, a trimethylcyclopentadienyl group, a tetramethylcyclopentadienyl group, an ethylcyclopentadienyl group, an n-propylcyclopentadienyl group, an isopropylcyclopentadienyl group, an n-butylcyclopentadienyl group, a sec-butylcyclopentadienyl group, a tert-butylcyclopentadienyl group, an n-pentylcyclopentadienyl group, a neopentylcyclopentadienyl group, an n-hexylcyclopentadienyl group, an n-octylcyclopentadienyl group, a tetrahydroindenyl group, an octahydrofluorenyl group, a phenylcyclopentadienyl group, a naphthylcyclopentadienyl group, a trimethylsilylcyclopentadienyl group, a triethylsilylcyclopentadienyl group, a triphenylsilylcyclopentadienyl group, a tert-butyldimethylsilylcyclopentadienyl group, and the like.

Further examples thereof include those groups in which both pairs of $R^1$ with $R^2$ and $R^3$ with $R^4$ or either one pair of $R^1$ with $R^2$ and $R^3$ with $R^4$ is/are bonded to form an aromatic ring optionally containing a hetero atom, and groups in which both pairs of $R^1$ with $R^2$ and $R^3$ with $R^4$ are bonded to form fluoren which may be substituted.

Specific examples thereof include indenyl groups which may be substituted such as an indenyl group, a methylindenyl group, a dimethylindenyl group, an ethylindenyl group, an n-propylindenyl group, an isopropylindenyl group, an n-butylindenyl group, a sec-butylindenyl group, a tert-butylindenyl group, an n-pentylindenyl group, a neopentylindenyl group, an n-hexylindenyl group, an n-octylindenyl group, an n-decylindenyl group, a phenylindenyl group, a methylphenylindenyl group, or a naphthylindenyl group; and fluorenyl groups which may be substituted such as a fluorenyl group, a 2-methylfluorenyl group, a 2,7-dimethylfluorenyl group, a 2-ethylfluorenyl group, a 2,7-diethylfluorenyl group, a 2-n-propylfluorenyl group, a 2,7-di-n-propylfluorenyl group, a 2-isopropylfluorenyl group, a 2,7-diisopropylfluorenyl group, a 2-n-butylfluorenyl group, a 2-sec-butylfluorenyl group, a 2-tert-butylfluorenyl group, a 2,7-di-n-butylfluorenyl group, a 2,7-di-sec-butylfluorenyl group, a 2,7-di-tert-butylfluorenyl group, 3,6-di-tert-butylfluorenyl group, a 2-n-pentylfluorenyl group, a 2-neopentylfluorenyl group, a 2-n-hexylfluorenyl group, a 2-n-octylfluorenyl group, a 2-n-decylfluorenyl group, a 2-n-dodecylfluorenyl group, a 2-phenylfluorenyl group, a 2,7-di-phenylfluorenyl group, a 2-methylphenylfluorenyl group, a 2-naphthylfluorenyl group, a 6,6,9,9-tetramethyl-6,7,8,9-tetrahydrobenzofluorenyl group, a 2,2,5,5,8,8,11,11-octamethyl-2,3,4,5,8,9,10,11-octahydrodibenzofluorenyl group.

Preferred are a cyclopentadienyl group, a methylcyclopentadienyl group, a tert-butylcyclopentadienyl group, a tetramethylcyclopentadienyl group, an indenyl group, a fluorenyl group, a 2,7-di-tert-butylfluorenyl group, a 3,6-di-tert-butylfluorenyl group, and the like.

In the production process of the present invention, the compounds having fluorenyl group which may be substituted provide particularly favorable results.

Examples of a Group 14 element in a periodic table denoted by A in the titanium halide complex (1) and the alkoxy-titanium complex (2) include, for example, a carbon atom, a silicon atom, a germanium atom and the like, and preferred is a silicon atom.

In substituent groups $R^1$, $R^2$, $R^3$, $R^4$, $R^5$, $R^6$, $R^7$, $R^8$, $R^9$, and $R^{10}$ of the titanium halide complex (1) and the alkoxy-titanium complex (2), examples of the halogen atom are a fluorine atom, a chlorine atom, a bromine atom, an iodine atom and the like, and preferred is a chlorine atom.

Specific examples of the $C_{1-20}$ alkyl group in $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ include, a methyl group, an ethyl group, an n-propyl group, an isopropyl group, an n-butyl group, a sec-butyl group, a tert-butyl group, an n-pentyl group, a neopentyl group, an amyl group, an n-hexyl group, a heptyl group, an n-octyl group, an n-nonyl group, an n-decyl group, an n-dodecyl group, an n-tridecyl group, a tetradecyl group, a pentadecyl group, a hexadecyl group, a heptadecyl group, an octadecyl group, a nonadecyl group, and an n-eicosyl group.

Specific examples of the halogen-substituted $C_{1-20}$ alkyl group in $R^1$, $R^2$, $R^3$, $R^4$, $R^5$, $R^6$, $R^7$, $R^8$, $R^9$, $R^{10}$, $R^{11}$, $R^{12}$, and $R^{14}$ include a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoropropyl group, a perfluorobutyl group, a pefluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, a perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group, a perbromoeicosyl group and the like, and preferred are a methyl group, an ethyl group, an isopropyl group, a tert-butyl group, an amyl group and the like.

Specific examples of the $C_{7-20}$ aralkyl group in $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ include, a benzyl group, a (2-methylphenyl)methyl group, a (3-methylphenyl)methyl group, a (4-methylphenyl)methyl group, a (2,3-dimethylphenyl)methyl group, a (2,4-dimethylphenyl) methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl) methyl group, a (2,3,6-trimethylphenyl)methyl group, a (3,4,5-trimethylphenyl)methyl group, a (2,4,6-trimethylphenyl) methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, an (n-propylphenyl) methyl group, an (isopropylphenyl)methyl group, an (n-butylphenyl)methyl group, a (sec-butylphenyl)methyl group, a (tert-butylphenyl)methyl group, an (n-pentylphenyl)methyl group, a-(neopentylphenyl)methyl group, an (n-hexylphenyl) methyl group, an (n-octylphenyl)methyl group, an (n-decylphenyl)methyl group, an (n-decylphenyl)methyl group, a naphthylmethyl group, an anthracenylmethyl group and the like. A benzyl group is preferable.

Specific examples of the halogen-substituted $C_{7-20}$ aralkyl group in $R^1$, $R^2$, $R^3$, $R^4$, $R^5$, $R^6$, $R^7$, $R^8$, $R^9$, $R^{10}$, $R^{11}$, $R^{12}$, and $R^{14}$ include those groups composed by the aralkyl group as exemplified above and halogen such as a fluorine atom, a chlorine atom, a bromine atom, or an iodine atom.

Specific examples of the $C_{6-20}$ aryl group in $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, an n-propylphenyl group, an isopropylphenyl group, an n-butylphenyl group, a sec-butylphenyl group, a tert-butylphenyl group, an n-pentylphenyl group, a neopentylphenyl group, an n-hexylphenyl group, an n-octylphenyl group, an n-decylphenyl group, an n-dodecylphenyl group, an n-tetradecylphenyl group, a naphthyl group, an anthracenyl group and the like. Preferred is a phenyl group.

Specific examples of the halogen-substituted $C_{6-20}$ aryl group in $R^1$, $R^2$, $R^3$, $R^4$, $R^5$, $R^6$, $R^7$, $R^8$, $R^9$, $R^{10}$, $R^{11}$, $R^{12}$ and $R^{14}$ include those composed by the $C_{6-20}$ aryl group as exemplified above and halogen such as a fluorine atom, a chlorine atom, a bromine atom, or an iodine atom.

Specific examples of the hydrocarbon group of the hydrocarbon-substituted silyl group in $R^1$, $R^2$, $R^3$, $R^4$, $R^5$, $R^6$, $R^7$, $R^8$, $R^9$, and $R^{10}$ include a $C_{1-10}$ alkyl group such as a methyl group, an ethyl group, an n-propyl group, an isopropyl group, an n-butyl group, a sec-butyl group, a tert-butyl group, an isobutyl group, an n-pentyl group, an n-hexyl group, a cyclohexyl group, an n-heptyl group, an n-octyl group, an n-nonyl group, and an n-decyl group and an aryl group such as a phenyl group, and the like.

Specific examples of the silyl group substituted with $C_{1-20}$ hydrocarbon group include mono-$C_{1-20}$ hydrocarbon-substituted silyl groups such as a methylsilyl group, an ethylsilyl group, and a phenylsilyl group;

di-$C_{1-20}$ hydrocarbon-substituted silyl groups such as a dimethylsilyl group, a diethylsilyl group, and a diphenylsilyl group; and tri-$C_{1-20}$ hydrocarbon-substituted silyl groups such as a trimethylsilyl group, a triethylsilyl group, a tri-n-propylsilyl group, a triisopropylsilyl group, a tri-n-butylsilyl group, a tri-sec-butylsilyl group, a tri-tert-butylsilyl group, a tri-isobutylsilyl group, a tert-butyl-dimethylsilyl group, a tri-n-pentylsilyl group, a tri-n-hexylsilyl group, a tricyclohexylsilyl group, and a triphenylsilyl group, and preferably a trimethylsilyl group, a tert-butyldimethylsilyl group, a triphenylsilyl group or the like. Examples of the hydrocarbon group composing these substituted silyl groups include the hydrocarbon group as exemplified above and halogen-substituted hydrocarbon groups composed by the hydrocarbon and halogen such as a fluorine atom, a chlorine atom, a bromine atom, or an iodine atom.

Specific examples of the $C_{1-20}$ alkoxy group in $R^1$, $R^2$, $R^3$, $R^4$, $R^5$, $R^6$, $R^7$, $R^8$, $R^9$, and $R^{10}$ include a methoxy group, an ethoxy group, an n-propoxy group, an isopropoxy group, an n-butoxy group, a sec-butoxy group, a tert-butoxy group, an n-pentyloxy group, a neopentyloxy group, an n-hexyloxy group, an n-octyloxy group, an n-nonyloxy group, an n-decyloxy group, an n-dodecyloxy group, an n-undecyloxy group, an n-dodecyloxy group, a tridecyloxy group, a tetradecyloxy group, an n-pentadecyloxy group, a hexadecyloxy group, a heptadecyloxy group, an octadecyloxy group, a nonadecyloxy group, an n-eicosyloxy group and the like, and preferred is a methoxy group, an ethoxy group, and a tert-butoxy group. Specific examples of the halogen-substituted $C_{1-20}$ alkoxy group are those groups composed by the alkoxy groups as exemplified above and halogen atom such as a fluorine atom, a chlorine atom, a bromine atom, or an iodine atom.

Specific examples of the $C_{7-20}$ aralkyloxy group in $R^1$, $R^2$, $R^3$, $R^4$, $R^5$, $R^6$, $R^7$, $R^8$, $R^9$, and $R^{10}$ include a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl) methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, an (n-propylphenyl)methoxy group, an (isopropylphenyl)methoxy group, an (n-butylphenyl)methoxy group, a (sec-butylphenyl)methoxy group, a (tert-butylphenyl)methoxy group, an (n-hexylphenyl)methoxy group, an (n-octylphenyl)methoxy group, an (n-decylphenyl)methoxy group, a naphthylmethoxy group, an anthracenylmethoxy group and the like, and preferred is a benzoyloxy group. Specific examples of the halogen-substituted $C_{7-20}$ aralkyloxy group include those groups composed by the aralkyloxy groups exemplified above and halogen such as a fluorine atom, a chlorine atom, a bromine atom, or an iodine atom.

Specific examples of the $C_{6-20}$ aryloxy group in $R^1$, $R^2$, $R^3$, $R^4$, $R^5$, $R^6$, $R^7$, $R^8$, $R^9$, and $R^{10}$ include a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, an n-propylphenoxy group, an isopropylphenoxy group, an n-butylphenoxy group, a sec-butylphenoxy group, a tert-butylphenoxy group, an n-hexylphenoxy group, an n-octylphenoxy group, an n-decylphenoxy group, an n-tetradecylphenoxy group, a naphthoxy group, an anthracenoxy group and the like. Specific examples of the halogen-substituted $C_{6-20}$ aryloxy group are those composed by $C_{6-20}$ aryloxy groups exemplified above and halogen such as a fluorine atom, a chlorine atom, a bromine atom, or an iodine atom.

The $C_{1-20}$ hydrocarbon-substituted amino group in $R^1$, $R^2$, $R^3$, $R^4$, $R^5$, $R^6$, $R^7$, $R^8$, $R^9$, and $R^{10}$ means an amino group substituted by two hydrocarbon groups, and specific examples of the hydrocarbon groups include $C_{1-20}$ alkyl groups such as a methyl group, an ethyl group, an n-propyl group, an isopropyl group, a n-butyl group, a sec-butyl group, a tert-butyl group, an isobutyl group, an n-pentyl group, an n-hexyl group, and a cyclohexyl group, and an aryl group such as a phenyl group, and the like, and these substituent groups may be bonded with one another to form a ring. Specific examples of the amino group substituted by $C_{1-20}$ hydrocarbon groups include a dimethylamino group, diethylamino group, a di-n-propylamino group, a diisopropylamino group, a di-n-butylamino group, a di-sec-butylamino group, a di-tert-butylamino group, a diisobutylamino group, a tert-butylisopropylamino group, a di-n-hexylamino group, a di-n-octylamino group, a di-n-decylamino group, a diphenylamino group, a bistrimethylsilylamino group, a bis-tert-butyldimethylsilylamino group, a pyrrolyl group, a pyrrolidinyl group, a piperidinyl group, a carbazolyl group, a dihydroindolyl group, a dihydroisoindolyl group and the like, and preferred are a dimethylamino group, a diethylamino group, a pyrrolidinyl group, a piperidinyl group, or the like.

The $C_{1-20}$ hydrocarbon-substituted silyloxy group in $R^1$, $R^2$, $R^3$, and $R^4$ means a silyloxy group substituted by three hydrocarbon groups, and specific examples of the hydrocarbon groups are the above-mentioned $C_{1-20}$ alkyl groups such as a methyl group, an ethyl group, an n-propyl group, an isopropyl group, an n-butyl group, a sec-butyl group, a tert-butyl group, an isobutyl group, an n-pentyl group, an n-hexyl group, and a cyclohexyl group, and an aryl group such as a phenyl group, and the like, and these substituent groups may be bonded with one another to form a ring. Specific examples of the silyloxy group substituted by $C_{1-20}$ hydrocarbon groups include a trimethylsilyloxy group, a triethylsilyloxy group, a tri-n-butylsilyloxy group, a triphenylsilyloxy group, a triisopropylsilyloxy group, a tert-butyldimethylsilyloxy group, a dimethylphenylsilyloxy group, a methyldiphenylsilyloxy group and the like, and preferably a trimethylsilyloxy group, a triphenylsilyloxy group, and a triisopropylsilyloxy group.

The $C_{1-20}$ hydrocarbon-substituted phosphino group in $R^1$, $R^2$, $R^3$, and $R^4$ means a phosphino group substituted by two hydrocarbon groups, and specific examples of the hydrocarbon groups include $C_{1-20}$ alkyl groups such as a methyl group, an ethyl group, an n-propyl group, an isopropyl group, an n-butyl group, a sec-butyl group, a tert-butyl group, an isobutyl group, an n-pentyl group, an n-hexyl group, a cyclohexyl group, a heptyl group, an n-octyl group, an n-nonyl group, an n-decyl group, an n-dodecyl group, an n-tridecyl group, a tetradecyl group, a pentadecyl group, a hexadecyl group, a heptadecyl group, an octadecyl group, a nonadecyl group, or an n-eicosyl group; and an aryl group such as a phenyl group, and the like, and these substituent groups may be bonded with one another to form a ring. Specific examples of the phosphino group substituted by $C_{1-20}$ hydrocarbon groups include a dimethylphosphino group, a diethylphosphino group, a di-n-propylphosphino group, a diisopropylphosphino group, a di-n-butylphosphino group, a di-sec-butylphosphino group, a di-tert-butylphosphino group, a diisobutylphosphino group, a tert-butylisopropylphosphino group, a di-n-hexylphosphino group, a di-n-octylphosphino group, a di-n-decylphosphino group, a diphenylphosphino group, a bistrimethylsilylphosphino group, a bis-tert-butyldimethylsilylphosphino group and the like, and preferably a dimethylphosphino group, a diethylphosphino group, and a diphenylphosphino group.

Examples of the hydrocarbon group of the $C_{1-20}$ hydrocarbon-substituted thio group in $R^1$, $R^2$, $R^3$, and $R^4$ include $C_{1-20}$ alkyl group such as a methyl group, an ethyl group, an n-propyl group, an isopropyl group, an n-butyl group, a sec-butyl group, a tert-butyl group, an isobutyl group, an n-pentyl group, an n-hexyl group, and a cyclohexyl group, an aryl group such as a phenyl group, and the like, and these substituent groups may be bonded with one another to form a ring or thiophene.

Specific examples of the thio group substituted by the $C_{1-20}$ hydrocarbon group include a methylthio group, an ethylthio group, an n-propylthio group, an isopropylthio group, an n-butylthio group, a sec-butylthio group, a tert-butylthio group, an isobutylthio group, an n-hexylthio group, an n-octylthio group, an n-decylthio group, a phenylthio group, and the like.

Neighboring two substituent groups among $R^1$, $R^2$, $R^3$, and $R^4$ and neighboring two substituent groups among $R^7$, $R^8$, $R^9$, and $R^{10}$ may be arbitrarily bonded to form a ring, and $R^5$ and $R^6$ may be bonded to form a ring.

Examples of the rings formed by bonding neighboring two substituent groups among $R^1$, $R^2$, $R^3$, and $R^4$ include saturated or unsaturated hydrocarbon rings, and hetero-rings such as thiophene ring, thiazole ring, thiazoline ring, thiadiazole ring, pyridine ring or the like.

Examples of the rings formed by bonding neighboring two substituent groups among $R^7$, $R^8$, $R^9$, and $R^{10}$ or by bonding $R^5$ and $R^6$ include a $C_{1-20}$ hydrocarbon-substituted saturated or unsaturated hydrocarbon ring, and the like. Specific examples thereof include a cyclopropane ring, a cyclobutane ring, a cyclopentane ring, a cyclohexane ring, a cycloheptane ring, a cyclooctane ring, a benzene ring, a naphthalene ring, an anthracene ring, and the like.

The substituent groups $R^{11}$ and $R^{12}$ may be bonded to each other to form a ring, and specific examples of the ring include 1,2-dioxy groups such as an ethylenedioxy group, a methylethylenedioxy group, a 1,1-dimethylethylenedioxy group, a 1,2-dimethylethylenedioxy group, a 1,1,2-trimethylethylenedioxy group, a tetramethylethylenedioxy group, a phenylethylenedioxy group, a 1,1-diphenylethylenedioxy group, a 1,2-diphenylethylenedioxy group, a 1,1,2-triphenylethylenedioxy group, a tetraphenylethylenedioxy group, a cyclobutane-1,2-dioxy group, a cyclopentane-1,2-dioxy group, a cyclohexane-1,2-dioxy group, a cycloheptane-1,2-dioxy group, and a cyclooctane-1,2-dioxy group; and 1,3-dioxy groups such as a propylene-1,3-dioxy group, a 1-methylpropylene-1,3-dioxy group, a 2-methylpropylene-1,3-dioxy group, a 1,1-dimethylpropylene-1,3-dioxy group, a 1,2-dimethylpropylene-1,3-dioxy group, a 1,3-dimethylpropylene-1,3-dioxy group, a 2,2-dimethylpropylene-1,3-dioxy group, a 1,1,2-trimethylpropylene-1,3-dioxy group, a 1,1,3-trimethylpropylene-1,3-dioxy group, a 1,2,2-trimethylpropylene-1,3-dioxy group, a 1,2,3-trimethylpropylene-1,3-dioxy group, a 1,1,2,2-tetramethylpropylene-1,3-dioxy group, a 1,1,2,3-tetramethylpropylene-1,3-dioxy group, a 1,1,3,3-tetramethylpropylene-1,3-dioxy group, a 1,2,2,3-tetramethylpropylene-1,3-dioxy group, a 1,1,2,2,3-pentamethylpropylene-1,3-dioxy group, a 1,1,2,3,3-pentamethylpropylene-1,3-dioxy group, a 1,1,2,2,3,3-hexamethylpropylene-1,3-dioxy group, a 1-phenylpropylene-1,3-dioxy group, a 2-phenylpropylene-1,3-dioxy group, a 1,1-diphenylpropylene-1,3-dioxy group, a 1,2-diphenylpropylene-1,3-dioxy group, a 1,3-diphenylpropylene-1,3-dioxy group, a 2,2-diphenylpropylene-1,3-dioxy group, a 1,1,2-triphenylpropylene-1,3-dioxy group, a 1,1,3-triphenylpropylene-1,3-dioxy group, a 1,2,2-triphenylpropylene-1,3-dioxy group, a 1,2,3-triphenylpropylene-1,3-dioxy group, a 1,1,2,2-tetraphenylpropylene-1,3-dioxy group, a 1,1,2,3-tetraphenylpropylene-1,3-dioxy group, a 1,1,3,3-tetraphenylpropylene-1,3-dioxy group, a 1,2,2,3-tetraphenylpropylene-1,3-dioxy group, a 1,1,2,2,3-pentaphenylpropylene-1,3-dioxy group, a 1,1,2,3,3-pentaphenylpropylene-1,3-dioxy group, and a 1,1,2,2,3,3-hexaphenylpropylene-1,3-dioxy group, and also include all of their stereoisomers and optical isomers.

Examples of the alkoxy-titanium complex (2) that can be obtainable in the present invention include, for example, dimethylsilylene(cyclopentadienyl)(2-phenoxy)titanium dimethoxide, dimethylsilylene(cyclopentadienyl)(3,4-dimethyl-2-phenoxy)titanium dimethoxide, dimethylsilylene(cyclopentadienyl)(3-tert-butyl-5-methyl-2-phenoxy)titanium dimethoxide, dimethylsilylene(cyclopentadienyl)(3-tert-butyl-5-methoxy-2-phenoxy)titanium dimethoxide, dimethylsilylene(cyclopentadienyl)(3-tert-butyl-5-dimethylamino-2-phenoxy)titanium dimethoxide, dimethylsilylene(cyclopentadienyl)(3-tert-butyl-2-phenoxy)titanium dimethoxide, dimethylsilylene(cyclopentadienyl)(3-tert-butyl-5-chloro-2-phenoxy)titanium dimethoxide, dimethylsilylene(cyclopentadienyl)(3-phenyl-2-phenoxy)titanium dimethoxide, dimethylsilylene(cyclopentadienyl)(3-tert-butyldimethylsilyl-5-methyl-2-phenoxy)titanium dimethoxide, dimethylsilylene(cyclopentadienyl)(3-trimethylsilyl-5-methyl-2-phenoxy)titanium dimethoxide, dimethylsilylene(cyclopentadienyl)(2-naphthoxy)titanium dimethoxide, dimethylsilylene(2,3,4,5-tetramethylcyclopentadienyl)(2-phenoxy)titanium dimethoxide, dimethylsilylene(2,3,4,5-tetramethylcyclopentadienyl)(3,4-dimethyl-2-phenoxy)titanium dimethoxide, dimethylsilylene(2,3,4,5-tetramethylcyclopentadienyl)(3-tert-butyl-5-methyl-2-phenoxy)titanium dimethoxide, dimethylsilylene(2,3,4,5-tetramethylcyclopentadienyl)(3-tert-butyl-5-methoxy-2-phenoxy)titanium dimethoxide, dimethylsilylene(2,3,4,5-tetramethylcyclopentadienyl)(3-tert-butyl-5-dimethylamino-2-phenoxy)titanium dimethoxide, dimethylsilylene(2,3,4,5-tetramethylcyclopentadienyl)(3-tert-butyl-2-phenoxy)titanium dimethoxide, dimethylsilylene(2,3,4,5-tetramethylcyclopentadienyl)(3-tert-butyl-5-chloro-2-phenoxy)titanium dimethoxide, dimethylsilylene(2,3,4,5-tetramethylcyclopentadienyl)(3-phenyl-2-phenoxy)titanium dimethoxide, dimethylsilylene(2,3,4,5-tetramethylcyclopentadienyl)(3-tert-butyldimethylsilyl-5-methyl-2-phenoxy)titanium dimethoxide, dimethylsilylene(2,3,4,5-tetramethylcyclopentadienyl)(3-trimethylsilyl-5-methyl-2-phenoxy)titanium dimethoxide, dimethylsilylene(2,3,4,5-tetramethylcyclopentadienyl)(2-naphthoxy)titanium dimethoxide, dimethylsilylene(indenyl)(2-phenoxy)titanium dimethoxide, dimethylsilylene(indenyl)(3,4-dimethyl-2-phenoxy)titanium dimethoxide, dimethylsilylene(indenyl)(3-tert-butyl-5-methyl-2-phenoxy)-titanium dimethoxide, dimethylsilylene(indenyl)(3-tert-butyl-5-methoxy-2-phenoxy)titanium dimethoxide, dimethylsilylene(indenyl)(3-tert-butyl-5-dimethylamino-2-phenoxy)titanium titanium dimethoxide, dimethylsilylene(indenyl)(3-tert-butyl-2-phenoxy)titanium dimethoxide, dimethylsilylene(indenyl)(3-tert-butyl-5-chloro-2-phenoxy)-titanium dimethoxide, dimethylsilylene(indenyl)(3-phenyl-2-phenoxy)titanium dimethoxide, dimethylsilylene(indenyl)(3-tert-butyldimethylsilyl-5-methyl-2-phenoxy)titanium dimethoxide, dimethylsilylene(indenyl)(3-trimethylsilyl-5-methyl-2-phenoxy)titanium dimethoxide, dimethylsilylene(indenyl)(2-naphthoxy)titanium dimethoxide, dimethylsilylene(2,7-di-tert-butyl-fluoren-9-yl)(2-phenoxy)titanium dimethoxide, dimethylsilylene(2,7-di-tert-butyl-fluoren-9-yl)(3,4-dimethyl-2-phenoxy)titanium dimethoxide, dimethylsilylene(2,7-di-tert-butyl-fluoren-9-yl)(3-tert-butyl-5-methyl-2-phenoxy)titanium dimethoxide, dimethylsilylene(2,7-di-tert-butyl-fluoren-9-yl)(3-tert-butyl-5-methoxy-2-phenoxy)titanium dimethoxide, dimethylsilylene(2,7-di-tert-butyl-fluoren-9-yl)(3-tert-butyl-5-dimethylamino-2-phenoxy)titanium dimethoxide, dimethylsilylene(2,7-di-tert-butyl-fluoren-9-yl)(3-tert-butyl-2-phenoxy)titanium dimethoxide, dimethylsilylene(2,7-di-tert-butyl-fluoren-9-yl)(3-tert-butyl-5-chloro-2-phenoxy)titanium dimethoxide, dimethylsilylene(2,7-di-tert-butyl-fluoren-9-yl)(3phenyl-2-phenoxy)titanium dimethoxide, dimethylsilylene(2,7-di-tert-butyl-fluoren-9-yl)(3-tert-butyldimethylsilyl-5-methyl-2-phenoxy)titanium dimethoxide, dimethylsilylene(2,7-di-tert-butyl-fluoren-9-yl)(3-tri-methylsilyl-5-methyl-2-phenoxy)titanium dimethoxide, dimethylsilylene(2,7-di-tert-butyl-fluoren-9-yl)(2-naphthoxy)titanium dimethoxide, dimethylsilylene(3,6-di-tert-butyl-fluoren-9-yl)(2-phenoxy)titanium dimethoxide, dimethylsilylene(3,6-di-tert-butyl-fluoren-9-yl)(3,4-di-methyl-2-phenoxy)titanium dimethoxide, dimethylsilylene(3,6-di-tert-butyl-fluoren-9-yl)(3-tert-butyl-5-methyl-2-phenoxy)titanium dimethoxide, dimethylsilylene(3,6-di-tert-butyl-fluoren-9-yl)(3-tert-butyl-5-methoxy-2-phenoxy)titanium dimethoxide, dimethylsilylene(3,6-di-tert-butyl-fluoren-9-yl)(3-tert-butyl-5-dimethylamino-2-phenoxy)titanium dimethoxide, dimethylsilylene(3,6-di-tert-butyl-fluoren-9-yl)(3-tert-butyl-2-phenoxy)titanium dimethoxide, dimethylsilylene(3,6-di-tert-butyl-fluoren-9-yl)(3-tert-butyl-5-chloro-2-phenoxy)titanium dimethoxide, dimethylsilylene(3,6-di-tert-butyl-fluoren-9-yl)(3-phenyl-2-phenoxy)titanium dimethoxide, dimethylsilylene(3,6-di-tert-butyl-fluoren-9-yl)(3-tert-butyldimethylsilyl-5-methyl-2-phenoxy)titanium dimethoxide, dimethylsilylene(3,6-di-tert-butyl-fluoren-9-yl)(3-tri-methylsilyl-5-methyl-2-phenoxy)titanium dimethoxide, dimethylsilylene(3,6-di-tert-butyl-fluoren-9-yl)(2-naphthoxy)titanium dimethoxide and the like, and also include those obtained by replacing the dimethylsilylene with diethylsilylene, diphenylsilylene, ethylmethylsilylene, methylphenylsilylene or the like and replacing dimethoxide with diethoxide, dipropoxide, diisopropoxide, dibutoxide, ethylenedioxide, 1,2-diphenylethylenedioxide, cyclohexane-1,2-dioxide, dibenzyloxide or the like.

The alkoxy-titanium complex (2) can be produced by reacting an alkaline earth metal alkoxide with the titanium halide complex (1).

The substituent groups $X^1$ and $X^2$ in the titanium halide complex (1) and the halogen defined by $X^3$ in the magnesium compound (3) may be fluorine, chlorine, bromine, iodine or the like, and preferred is a chlorine atom.

The titanium halide complex (1) can be produced by reacting a corresponding cyclopentadiene compound with a base according to a conventionally known technique (e.g., see Patent Document 4) and successively reacting the reaction product with a transition metal compound.

Examples of the titanium halide complex (1) include, for example, dimethylsilylene(cyclopentadienyl)(2-phenoxy)titanium dichloride, dimethylsilylene(cyclopentadienyl)(3,4-dimethyl-2-phenoxy)titanium dichloride, dimethylsilylene(cyclopentadienyl)(3-tert-butyl-5-methyl-2-phenoxy)titanium dichloride, dimethylsilylene(cyclopentadienyl)(3-tert-butyl-5-methoxy-2-phenoxy)titanium dichloride, dimethylsilylene(cyclopentadienyl)(3-tert-butyl-5-dimethylamino-2-phenoxy)titanium dichloride, dimethylsilylene(cyclopentadienyl)(3-tert-butyl-2-phenoxy)titanium dichloride, dimethylsilylene(cyclopentadienyl)(3-tert-butyl-5-chloro-2-phenoxy)titanium dichloride, dimethylsilylene(cyclopentadienyl)(3-phenyl-2-phenoxy)titanium dichloride, dimethylsilylene(cyclopentadienyl)(3-tert-butyldimethylsilyl-5-methyl-2-phenoxy)titanium dichloride, dimethylsilylene(cyclopentadienyl)(3-trimethylsilyl-5-methyl-2-phenoxy) titanium dichloride, dimethylsilylene(cyclopentadienyl)(2-naphthoxy)titanium dichloride, dimethylsilylene(2,3,4,5-tetramethylcyclopentadienyl)(2-phenoxy)titanium dichloride, dimethylsilylene(2,3,4,5-tetramethylcyclopentadienyl)(3,4-dimethyl-2-phenoxy)titanium dichloride, dimethylsilylene(2,3,4,5-tetramethylcyclopentadienyl)(3-tert-butyl-5-methyl-2-phenoxy)titanium dichloride, dimethylsilylene(2,3,4,5-tetramethylcyclopentadienyl)(3-tert-butyl-5-methoxy-2-phenoxy)titanium dichloride, dimethylsilylene(2,3,4,5-tetramethylcyclopentadienyl)(3-tert-butyl-5-dimethylamino-2-phenoxy)titanium dichloride, dimethylsilylene(2,3,4,5-tetramethylcyclopentadienyl)(3-tert-butyl-2-phenoxy)titanium dichloride, dimethylsilylene(2,3,4,5-tetramethylcyclopentadienyl)(3-tert-butyl-5-chloro-2-phenoxy)titanium dichloride, dimethylsilylene(2,3,4,5-tetramethylcyclopentadienyl)(3-phenyl-2-phenoxy) titanium dichloride, dimethylsilylene(2,3,4,5-tetramethylcyclopentadienyl)(3-tert-butyldimethylsilyl-5-methyl-2-phenoxy)titanium dichloride, dimethylsilylene(2,3,4,5-tetramethylcyclopentadienyl)(3-trimethylsilyl-5-methyl-2-phenoxy)titanium dichloride, dimethylsilylene(2,3,4,5-tetramethylcyclopentadienyl)(2-naphthoxy)titanium dichloride, dimethylsilylene(indenyl)(2-phenoxy)titanium dichloride, dimethylsilylene(indenyl)(3,4-dimethyl-2-phenoxy)titanium dichloride, dimethylsilylene(indenyl)(3-tert-butyl-5-methyl-2-phenoxy)titanium dichloride, dimethylsilylene(indenyl)(3-tert-butyl-5-methoxy-2-phenoxy)titanium dichloride, dimethylsilylene(indenyl)(3-tert-butyl-5-dimethylamino-2-phenoxy)titanium dichloride, dimethylsilylene(indenyl)(3-tert-butyl-2-phenoxy)titanium dichloride, dimethylsilylene(indenyl)(3-tert-butyl-5-chloro-2-phenoxy)-titanium dichloride, dimethylsilylene(indenyl)(3-phenyl-2-phenoxy)titanium dichloride, dimethylsilylene(indenyl)(3-tert-butyldimethylsilyl-5-methyl-2-phenoxy)titanium dichloride, dimethylsilylene(indenyl)(3-trimethylsilyl-5-methyl-2-phenoxy)titanium dichloride, dimethylsilylene(indenyl)(2-naphthoxy)titanium dichloride, dimethylsilylene(2,7-di-tert-butylfluoren-9-yl)(2-phenoxy)titanium dichloride, dimethylsilylene(2,7-di-tert-butylfluoren-9-yl)(3,4-di-methyl-2-phenoxy)titanium dichloride, dimethylsilylene(2,7-di-tert-butylfluoren-9-yl)(3-tert-butyl-5-methyl-2-phenoxy)titanium dichloride, dimethylsilylene(2,7-di-tert-butylfluoren-9-yl)(3-tert-butyl-5-methoxy-2-phenoxy)titanium dichloride, dimethylsilylene (2,7-di-tert-butylfluoren-9-yl)(3-tert-butyl-5-dimethylamino-2-phenoxy)titanium dichloride, dimethylsilylene(2,7-di-tert-butylfluoren-9-yl)(3-tert-butyl-2-phenoxy)titanium dichloride, dimethylsilylene(2,7-di-tert-butylfluoren-9-yl)(3-tert-butyl-5-chloro-2-phenoxy)titanium dichloride, dimethylsilylene(2,7-di-tert-butylfluoren-9-yl)(3-phenyl-2-phenoxy)titanium dichloride, dimethylsilylene(2,7-di-tert-butylfluoren-9-yl)(3-tert-butyldimethylsilyl-5-methyl-2-phenoxy)titanium dichloride, dimethylsilylene(2,7-di-tert-butylfluoren-9-yl)(3-tri-methylsilyl-5-methyl-2-phenoxy) titanium dichloride, dimethylsilylene(2,7-di-tert-butylfluoren-9-yl)(2-naphthoxy)titanium dichloride, dimethylsilylene(3,6-di-tert-butylfluoren-9-yl)(2-phenoxy)titanium dichloride, dimethylsilylene(3,6-di-tert-butylfluoren-9-yl)(3,4-dimethyl-2-phenoxy)titanium dichloride, dimethylsilylene(3,6-di-tert-butylfluoren-9-yl)(3-tert-butyl-5-methyl-2-phenoxy)titanium dichloride, dimethylsilylene(3,6-di-tert-butylfluoren-9-yl)(3-tert-butyl-5-methoxy-2-phenoxy)titanium dichloride, dimethylsilylene (3,6-di-tert-butylfluoren-9-yl)(3-tert-butyl-5-dimethylamino-2-phenoxy)titanium dichloride, dimethylsilylene(3, 6-di-tert-butylfluoren-9-yl)(3-tert-butyl-2-phenoxy)titanium dichloride, dimethylsilylene(3,6-di-tert-butylfluoren-9-yl) (3-tert-butyl-5-chloro-2-phenoxy)titanium dichloride, dimethylsilylene(3,6-di-tert-butylfluoren-9-yl)(3-phenyl-2-phenoxy)titanium dichloride, dimethylsilylene(3,6-di-tert-butylfluoren-9-yl)(3-tert-butyldimethylsilyl-5-methyl-2-phenoxy)titanium dichloride, dimethylsilylene(3,6-di-tert-butylfluoren-9-yl)(3-tri-methylsilyl-5-methyl-2-phenoxy) titanium dichloride, dimethylsilylene(3,6-di-tert-butylfluoren-9-yl)(2-naphthoxy)titanium dichloride and the like, and also include those obtained by replacing the dimethylsilylene with diethylsilylene, diphenylsilylene, ethylmethylsilylene, or methylphenylsilylene and replacing chloride with fluoride, bromide, or iodide.

Examples of the alkaline earth metal alkoxide that can be used are magnesium dimethoxide, magnesium diethoxide, magnesium di-n-propoxide, magnesium diisopropoxide, magnesium di-n-butoxide, magnesium di-sec-butoxide, magnesium di-tert-butoxide, magnesium di-n-pentoxide, magnesium dineopentoxide, magnesium dimethoxyethoxide, magnesium diethoxyethoxide, magnesium dibenzyloxide, magnesium di-1-phenylethoxide, and those alkaline earth metal alkoxides in which magnesium is replaced with calcium, strontium, or barium and which are induced from monools; and also include magnesium ethylenedioxide, magnesium methylethylenedioxide, magnesium 1,2-dimethylethylenedioxide, magnesium tetramethylethylenedioxide, magnesium phenylethylenedioxide, magnesium 1,2-diphenylethylenedioxide, magnesium tetraphenylethylenedioxide, magnesium cyclopentane-1,2-dioxide, magnesium cyclohexane-1,2-dioxide, magnesium propylene-1,3-dioxide, magnesium 1,3-dimethylpropylene-1,3-dioxide, magnesium 1,3-diphenylpropylene-1,3-dioxide, and those alkaline earth metal alkoxides in which magnesium is arbitrarily replaced with calcium, strontium, or barium and which can be derivatized from diols; and also include all of their stereoisomers and optical isomers.

The compounds may be commercially available or they may be produced in situ by reacting an alcohol with an alkaline earth metal compound.

For example, the alkoxy-titanium complex (2) can be produced by reacting a magnesium compound of formula (3):

wherein $R^{13}$ denotes a $C_{1-20}$ alkyl group, a $C_{6-20}$ aryl group, or a $C_{7-20}$ aralkyl group, and $X^3$ denotes halogen, with an alcohol of formula (4):

wherein $R^{14}$ is same as $R^{11}$ or $R^{12}$, or represents a $C_{1-20}$ alkyl group which may be substituted by halogen, a $C_{6-20}$ aryl group which may be substituted by halogen, or a $C_{7-20}$ aralkyl group which may be substituted by halogen, to produce a magnesium alkoxide, and then reacting the resulting with a titanium halide complex (1).

Examples of the alkaline earth metal compound that can be used for producing the alkaline earth alkoxides in the system are Grignard reagents such as methylmagnesium chloride, phenylmagnesium chloride, benzylmagnesium chloride, methylmagnesium bromide, phenylmagnesium bromide, and benzylmagnesium bromide, and preferably methylmagnesium chloride, methylmagnesium bromide and the like.

Examples of the alcohol that can be used are monools such as methanol, ethanol, n-propanol, isopropanol, n-butanol, sec-butanol, tert-butanol, n-pentanol, neopentyl alcohol, ethylene glycol monomethyl ether, ethylene glycol monoethyl ether, phenol, benzyl alcohol, and 1-phenylethanol; and diols such as ethylene glycol, propylene glycol, 2,3-butanediol, tetramethylethylene glycol, phenylethylene glycol, hydrobenzoin, tetraphenylethylene glycol, cyclopentane-1,2-diol, cyclohexane-1,2-diol, 1,3-propanediol, 2,4-pentanediol, 1,3-diphenyl-1,3-propanediol, and tartaric acid, and also include all of their stereoisomers and optical isomers.

A method reaction is not particularly limited; however the reaction of a titanium halide complex with an alkaline earth metal alkoxide is carried out preferably in an inert atmosphere of nitrogen, argon or the like in the presence of a solvent.

The amount of the alkaline earth metal alkoxide that may be used is generally about 0.5 to 10 moles and preferably about 0.8 to 3 moles per mol of the titanium halide complex.

An aprotic polar solvent that can be used for the reaction is not particularly limited, and cyclic or acyclic ethers such as diethyl ether, dibutyl ether, methyl tert-butyl ether, tetrahydrofuran, and 1,4-dioxane may be exemplified, and preferred is tetrahydrofuran. The amount of the solvent is generally 1 to 200 parts by weight and preferably about 3 to 30 parts by weight per part by weight of the titanium halide complex.

Besides the polar solvent, another solvent may be used in combination. The another solvent are not particularly limited and examples thereof include aliphatic hydrocarbons such as pentane, hexane, heptane, octane, and decane; aromatic hydrocarbons such as benzene, toluene, xylene, and mesitylene; aliphatic halogenated hydrocarbons such as dichloromethane, chloroform, and dichloroethane; aromatic halogenated hydrocarbons such as monochlorobenzene and dichlorobenzene; and mixtures of these exemplified solvents.

The reaction temperature is generally from −100° C. to a boiling point of the solvent and preferably from about −80° C. to 30° C.

After the reaction, for example, an insoluble solid material is removed and the solvent is removed by distillation to obtain an alkoxy-titanium complex (2), or after a part of the reaction solvent is concentrated and an insoluble material is removed, an alkoxy-titanium complex (2) can be obtained from the filtrate. If necessary, the product can be purified by a conventional method such as recrystallization, sublimation or the like.

EXAMPLES

Hereinafter, the present invention will be described in more detail along with Examples, however it is not intended that the present invention be limited to the illustrated Examples.

The following measurement method was employed for characterization of chemical structures.

(1) Proton nuclear magnetic resonance spectrometry ($^1$H-NMR)

Apparatus: EX 270 manufactured by JEOL Ltd. or DPX-300 manufactured by Bruker

Sample cell; 5 mmφ tube

Measurement solvent: $CDCl_3$ or $C_6D_6$

Sample concentration: 10 mg/0.5 mL ($CDCl_3$ or $C_6D_6$)

Measurement temperature: room temperature (about 25° C.)

Measurement parameters: 5mmφ probe, MENUF NON, OBNUC $^1$H, number of integration 16 times Pulse angle: 45 degrees Repeated period: ACQTM 3 seconds, PD 4 seconds Internal standard: $CDCl_3$ (7.26 ppm), $C_6D_6$ (7.15 ppm)

(2) Mass spectrometry

[Electron ionization-mass spectrometry (EI-MS)]

Apparatus: JMS-AX505W manufactured by JEOL Ltd.

Ionization voltage: 70 eV

Ion source temperature: 230° C.

Data processing apparatus: MS-MP 8020D

MASS RANGE: m/z 35-1000

Example 1

Synthesis of (2-aryloxy-3-tert-butyl-5-methylphenyl)(2,7-di-tert-butylfluoren-9-yl)diethylsilane After potassium hydride (30 wt %, 3.00 g, 22.45 mmol) was washed with 6 mL of hexane three times under nitrogen, 37 mL of THF was added. A THF solution (32 mL) of 2,7-di-tert-butylfluorene (5.00 g, 17.96 mmol) was added dropwise at 0° C. to the obtained THF slurry of potassium hydride. After the mixture was stirred at room temperature for 2.5 hours, a toluene solution (7 mL) of (2-aryloxy-3-tert-butyl-5-methylphenyl)chlorodiethylsilane (5.84 g, 17.96 mmol) was added dropwise at −78° C. The obtained reaction mixture was heated to room temperature and stirred for 2.5 hours. The obtained reaction solution was added dropwise at 0° C. to a mixture of 32 mL of an aqueous 10% sodium hydrogen carbonate solution and 32 mL of an aqueous 10% sodium carbonate solution and the reaction product was extracted with 20 mL of toluene. After the product was dried over sodium sulfate, the solvent was concentrated under reduced pressure and (2-aryloxy-3-tert-butyl-5-methylphenyl)(2,7-di-tert-butylfluoren-9-yl)diethylsilane was obtained quantitatively.

$^1$H-NMR ($CDCl_3$, δ (ppm)): 0.42-0.64 (m, 6H), 0.72-1.00 (m, 4H), 1.25 (s, 18H), 1.43 (s, 9H), 2.28 (s, 3H), 4.39 (br s, 2H), 4.46 (s, 1H), 5.30 (d, J=10.4 Hz, 1H), 5.57 (d, J=17.3 Hz, 1H), 5.99-6.11 (m, 1H), 6.96 (s, 1H), 7.09-7.32 (m, 5H), 7.67 (d, J=8.0 Hz, 2H)

Synthesis of diethylsilylene(2,7-di-tert-butylfluoren-9-yl)(3-tert-butyl-5-methyl-2-phenoxy)titanium dichloride After a 1.57 M hexane solution (6.22 mL, 9.76 mmol) of n-butyl lithium was added dropwise at −78° C. to a toluene solution (45 mL) of (2-aryloxy-3-tert-butyl-5-methylphenyl)(2,7-di-tert-butylfluoren-9-yl)diethylsilane (2.46 g, 4.34 mmol), the mixture was stirred at room temperature for 2 hours. After a toluene solution (7 mL) of titanium tetrachloride (1.23 g, 6.51 mmol) was added dropwise at −78° C. to the reaction mixture and the mixture was heated to room temperature, the mixture was stirred at 95° C. for 3 hours. After the reaction mixture was cooled, the solvent was concentrated and the reaction product was filtered with hexane to remove insolubles. After the solvent was removed by distillation under reduced pressure, the reaction product was washed with pentane and diethylsilylene(2,7-di-tert-butylfluoren-9-yl)(3-tert-butyl-5-methyl-2-phenoxy)titanium dichloride (0.129 g, 4.8%) was obtained as a brown solid.

$^1$H-NMR ($C_6D_6$, δ ppm)): 1.06-1.13 (m, 6H), 1.20 (s, 18H), 1.29-1.51 (m, 4H), 1.37 (s, 9H), 2.26 (s, 3H), 7.21 (s, 1H), 7.37 (s, 1H), 7.45 (d, J=9.0 Hz, 2H), 7.80 (s, 2H), 8.00 (d, J=9.0 Hz, 2H)

Mass spectrometry (EI, m/z: 642 ($M^+$)

Synthesis of diethylsilylene(2,7-di-tert-butylfluoren-9-yl)(3-tert-butyl-5-methyl-2-phenoxy)titanium diethoxide Magnesium diethoxide (44.6 mg, 0.39 mmol) was added to a THF solution (4 mL) of diethylsilylene(2,7-di-tert-butylfluoren-9-yl)(3-tert-butyl-5-methyl-2-phenoxy)titanium dichloride (248.7 mg, 0.39 mmol) at room temperature in a Schlenk tube. After the mixture was stirred at room temperature for 24 hours, the solvent was concentrated. Hexane was added and insoluble materials were removed by filtration. The obtained filtrate was concentrated, pentane was added and the obtained precipitate was collected by filtration and dried to obtain diethylsilylene(2,7-di-tert-butylfluoren-9-yl)(3-tert-butyl-5-methyl-2-phenoxy)titanium diethoxide (180.9 mg, isolated yield. 70.3%) as a yellow solid.

$^1$H-NMR (CDCl$_3$, δ (ppm)): 0.59 (t, J=7.6 Hz, 6H), 0.82 (t, J=6.9 Hz, 6H), 0.83-1.28 (m, 4H), 1.27 (s, 18H), 1.39 (s, 9H), 2.34 (s, 3H), 3.81 (q, J=6.9 Hz, 4H), 7.04 (s, 1H), 7.18 (s, 1H), 7.25 (d, J=8.2 Hz, 2H), 7.62 (s, 2H), 7.80 (d, J=8.2 Hz, 2H)
Mass spectrometry (EI, m/z: 663 (M$^+$), 634, 590, 278, 263, 221

Example 2

Diethylsilylene(2,7-di-tert-butylfluoren-9-yl)(3-tert-butyl-5-methyl-2-phenoxy)titanium dichloride (208.3 mg, 0.31 mmol) and magnesium diethoxide (39.1 mg, 0.34 mmol) were mixed in a toluene/THF (10/1) solvent (4.4 mL) in a Schlenk tube. After the mixture was stirred at room temperature for 24 hours, the solvent was concentrated. Hexane was added and insoluble materials were removed by filtration. The obtained filtrate was concentrated, pentane was added and the obtained precipitate was collected by filtration and dried to obtain diethylsilylene(2,7-di-tert-butylfluoren-9-yl)(3-tert-butyl-5-methyl-2-phenoxy)titanium diethoxide (133.9 mg, isolated yield 65.0%) as a yellow solid.

Example 3

Synthesis of dimethylsilylene(indenyl)(3-tert-butyl-5-methyl-2-phenoxy)titanium diethoxide Magnesium diethoxide (83.3 mg, 0.73 mmol) was added to a THF solution (4 mL) of dimethylsilylene(indenyl)(3-tert-butyl-5-methyl-2-phenoxy)titanium dichloride (300.0 mg, 0.66 mmol) at room temperature in a Schlenk tube. After the mixture was stirred at room temperature for 12 hours, the solvent was concentrated. Hexane was added and insoluble materials were removed by filtration. The obtained filtrate was concentrated, pentane was added and the obtained precipitate was collected by filtration and dried to obtain dimethylsilylene(indenyl)(3-tert-butyl-5-methyl-2-phenoxy)titanium diethoxide (218.9 mg, isolated yield 70.0%) as a yellow solid.

$^1$H-NMR (CDCl$_3$, δ (ppm)): 0.54 (s, 3H), 0.64 (s, 3H), 0.80-1.00 (m, 3H), 1.14 (s, 9H), 1.18-1.45 (m, 3H), 2.35 (s, 3H), 3.80-4.00 (m, 2H), 4.30 (q, J=7.3 Hz, 2H), 6.76-6.80 (m, 2H), 6.93-7.00 (m, 1H), 7.08 (s, 1H), 7.10-7.20 (m, 3H), 7.74 (d, J=8.2 Hz, 1H)

Example 4

Synthesis of dimethylsilylene(2,3,4,5-tetramethylcyclopentadienyl)(3-tert-butyl-5-methyl-2-phenoxy)titanium diethoxide Magnesium diethoxide (82.2 mg, 0.72 mmol) was added to a THF solution (4 mL) of dimethylsilylene(2,3,4,5-tetramethylcyclopentadienyl)(3-tert-butyl-5-methyl-2-phenoxy)titanium dichloride (300.0 mg, 0.65 mmol) at room temperature in a Schlenk tube. After the mixture was stirred at room temperature for 12 hours, the solvent was concentrated. Hexane was added and insoluble materials were removed by filtration. The obtained filtrate was concentrated, pentane was added and the obtained precipitate was collected by filtration and dried to obtain dimethylsilylene(2,3,4,5-tetramethylcyclopentadienyl)(3-tert-butyl-5-methyl-2-phenoxy)titanium diethoxide (203.1 mg, isolated yield 65.0%) as a yellow solid.

$^1$H-NMR (CDCl$_3$, δ (ppm)): 0.49 (s, 6H), 1.14 (t, J=6.7 Hz, 6H), 1.35 (s, 9H), 1.96 (s, 6H), 2.07 (s, 6H), 2.30 (s, 3H), 4.33 (q, J=6.7 Hz, 4H), 7.08 (s, 1H), 7.10 (s, 1H)

Example 5

Synthesis of diethylsilylene(2,7-di-tert-butylfluoren-9-yl)(3-tert-butyl-5-methyl-2-phenoxy)titanium diphenoxide Methylmagnesium chloride (3.00 M, 683.6 mL, 2.05 mmol) was added dropwise to a THF solution (12 mL) of phenol (193.0 mg, 2.05 mmol) in a Schlenk tube and stirred at room temperature for 3 hours. After a THF solution (3 mL) of diethylsilylene(2,7-di-tert-butylfluoren-9-yl)(3-tert-butyl-5-methyl-2-phenoxy)titanium dichloride (600.0 mg, 0.93 mmol) was added dropwise at −20° C., the obtained mixture was stirred at room temperature for 20 hours. The solvent was concentrated, pentane was added and insoluble materials were removed by filtration. The obtained filtrate was concentrated, pentane was added and the obtained precipitate was collected by filtration and dried to obtain diethylsilylene(2,7-di-tert-butylfluoren-9-yl)(3-tert-butyl-5-methyl-2-phenoxy)titanium diphenoxide (599.9 mg, isolated yield 84.5%) as an orange solid.

$^1$H-NMR (CDCl$_3$, δ (ppm)): 0.81-1.43 (m, 10H), 1.16 (s, 18H), 1.17 (s, 9H), 2.41 (s, 3H), 6.39 (d, J=9.9 Hz, 4H), 6.70-6.80 (m, 2H), 7.00-7.34 (m, 8H), 7.57 (s, 2H), 7.71 (d, J=8.6 Hz, 2H)
Mass spectrometry (EI, m/z): 758 (M$^+$)

INDUSTRIAL APPLICABILITY

The alkoxy-titanium complex of formula (2) can be industrially advantageously produced according to the present invention and the obtained complex is useful as, for example, an olefin polymerization catalyst component.

The invention claimed is:
1. A process for producing an alkoxy-titanium complex of formula (2):

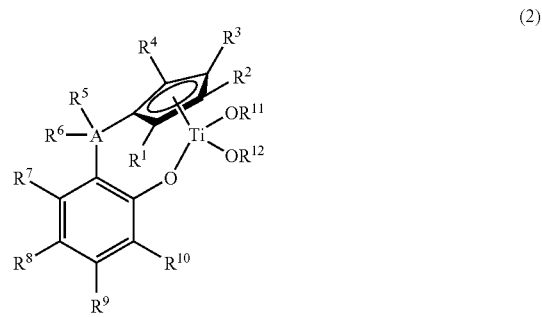

wherein A, $R^1$, $R^2$, $R^3$, $R^4$, $R^5$, $R^6$, $R^7$, $R^8$, $R^9$, and $R^{10}$ each denotes the same meaning as described below;
$R^{11}$ and $R^{12}$ are the same or different and denote a $C_{1-20}$ alkyl group which may be substituted by halogen,
a $C_{7-20}$ aralkyl group which may be substituted by halogen, or
a $C_{6-20}$ aryl group which may be substituted by halogen, and $R^{11}$ and $R^{12}$ may be bonded to form a ring,
which comprises reacting a magnesium compound of formula (3):

$$R^{13}MgX^3 \quad (3)$$

wherein $R^{13}$ denotes a $C_{1-20}$ alkyl group, a $C_{6-20}$ aryl group, or a $C_{7-20}$ aralkyl group, and $X^3$ denotes halogen, with an alcohol of formula (4):

$$R^{14}OH \quad (4)$$

wherein $R^{14}$ is the same as $R^{11}$ or $R^{12}$, and
reacting the resulting magnesium alkoxide with a titanium halide complex of formula (1):

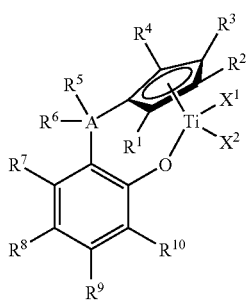

(1)

wherein A denotes a Group 14 element of the periodic table;
$R^1$, $R^2$, $R^3$, and $R^4$ are the same or different and denote a hydrogen atom, halogen,
a $C_{1-20}$ alkyl group which may be substituted by halogen,
a $C_{6-20}$ aryl group which may be substituted by halogen,
a $C_{7-20}$ aralkyl group which may be substituted by halogen,
a silyl group substituted by $C_{1-20}$ hydrocarbon which may be substituted by halogen,
a $C_{1-20}$ alkoxy group which may be substituted by halogen,
a $C_{6-20}$ aryloxy group which may be substituted by halogen,
a $C_{7-20}$ aralkyloxy group which may be substituted by halogen,
a silyloxy group substituted by $C_{1-20}$ hydrocarbon which may be substituted by halogen,
an amino group substituted by $C_{1-20}$ hydrocarbon which may be substituted by halogen,
a phosphino group substituted by $C_{1-20}$ hydrocarbon which may be substituted by halogen, or
a thio group substituted by $C_{1-20}$ hydrocarbon which may be substituted by halogen;
$R^5$, $R^6$, $R^7$, $R^8$, $R^9$, and $R^{10}$ are the same or different and denote a hydrogen atom, halogen,
a $C_{1-20}$ alkyl group which may be substituted by halogen,
a $C_{1-20}$ alkoxy group which may be substituted by halogen,
a $C_{6-20}$ aryl group which may be substituted by halogen,
a $C_{6-20}$ aryloxy group which may be substituted by halogen,
a $C_{7-20}$ aralkyl group which may be substituted by halogen,
a $C_{7-20}$ aralkyloxy group which may be substituted by halogen,
a silyl group substituted by $C_{1-20}$ hydrocarbon which may be substituted by halogen, or
an amino group substituted by $C_{1-20}$ hydrocarbon which may be substituted by halogen;
pairs of $R^1$ with $R^2$ and $R^3$ with $R^4$ are bonded to form fluorene, which may be substituted, and $R^5$ and $R^6$ may be bonded to form a ring; neighboring groups among $R^7$, $R^8$, $R^9$, and $R^{10}$ may be arbitrarily bonded to form a ring, and
$X^1$ and $X^2$ independently denote any halogen atom.

2. The process for producing an alkoxy-titanium complex according to claim 1, wherein the reaction is carried out in the presence of an aprotic polar solvent.

3. The process for producing an alkoxy-titanium complex according to claim 1, wherein A in the formulas (1) and (2) denotes a silicon atom.

4. The process for producing an alkoxy-titanium complex according to claim 1, wherein both pairs of $R^1$ with $R^2$ and $R^3$ with $R^4$ or either one pair of $R^1$ with $R^2$ and $R^3$ with $R^4$ of the cyclopentadiene ring is bonded to form an aromatic ring optionally containing a hetero atom.

5. The process for producing an alkoxy-titanium complex according to claim 1, wherein both pairs of $R^1$ with $R^2$ and $R^3$ with $R^4$ of a cyclopentadiene ring are bonded to form a fluorene which may be substituted.

* * * * *